US011065387B2

(12) United States Patent
Laiosa

(10) Patent No.: US 11,065,387 B2
(45) Date of Patent: Jul. 20, 2021

(54) ACTIVATION MECHANISM FOR A MEDICAMENT DELIVERY DEVICE AND A MEDICAMENT DELIVERY DEVICE USING THE ACTIVATION MECHANISM

(71) Applicant: SHL MEDICAL AG, Zug (CH)

(72) Inventor: John Laiosa, Lodi, NJ (US)

(73) Assignee: SHL MEDICAL AG, Zug (CH)

(*) Notice: Subject to any disclaimer, the term of this patent is extended or adjusted under 35 U.S.C. 154(b) by 482 days.

(21) Appl. No.: 15/775,105

(22) PCT Filed: Oct. 25, 2016

(86) PCT No.: PCT/EP2016/075646
§ 371 (c)(1),
(2) Date: May 10, 2018

(87) PCT Pub. No.: WO2017/080814
PCT Pub. Date: May 18, 2017

(65) Prior Publication Data
US 2018/0326152 A1 Nov. 15, 2018

(30) Foreign Application Priority Data
Nov. 13, 2015 (SE) .................................... 1551475-5

(51) Int. Cl.
*A61M 5/20* (2006.01)
*A61M 5/24* (2006.01)
*A61M 5/32* (2006.01)

(52) U.S. Cl.
CPC ............ *A61M 5/2033* (2013.01); *A61M 5/20* (2013.01); *A61M 5/24* (2013.01); *A61M 5/3204* (2013.01);
(Continued)

(58) Field of Classification Search
CPC .... A61M 2005/202; A61M 2005/2026; A61M 2005/2073; A61M 2005/208; A61M 5/20; A61M 5/2033; A61M 5/24; A61M 5/3204
See application file for complete search history.

(56) References Cited

U.S. PATENT DOCUMENTS 5,137,516 A    8/1992 Rand et al.

FOREIGN PATENT DOCUMENTS

CN          103764206 A      4/2014
DE      102005022532 A1      11/2006
(Continued)

OTHER PUBLICATIONS

International Search Report and Written Opinion for Int. App. No. PCT/EP2016/075646, dated Jan. 19, 2017.

*Primary Examiner* — Brandy S Lee
(74) *Attorney, Agent, or Firm* — McDonnell Boehnen Hulbert & Berghoff LLP

(57) ABSTRACT

An activation mechanism for a medicament delivery device is provided having a housing elongated along a generally longitudinal axis, a spring-biased drive member, a locking unit, movable from a locked position, preventing longitudinal movement of said drive member, to an unlocked position, a first activation member movable relative to the housing; a second activation member movable relative to the housing, and wherein the locking unit comprises a key member, movable relative to the locking unit, wherein the first activation member and the second activation member are configured to move the locking unit from the locked position to the unlocked position, wherein upon actuation, the first activation member and the second activation member cooperate in interacting with the key member to move (Continued)

the key member to the cooperating position and to move the locking unit from the locked position to the unlocked position.

20 Claims, 8 Drawing Sheets

(52) U.S. Cl.
CPC . *A61M 2005/202* (2013.01); *A61M 2005/208* (2013.01); *A61M 2005/2026* (2013.01); *A61M 2005/2073* (2013.01)

(56) References Cited

FOREIGN PATENT DOCUMENTS

| TW | 201102120 A | 1/2011 | |
|---|---|---|---|
| TW | 201529117 A | 8/2015 | |
| WO | 2010/066591 A1 | 6/2010 | |
| WO | 2011/005177 A1 | 1/2011 | |
| WO | 2015/028393 A1 | 3/2015 | |
| WO | WO-2015028393 A1 * | 3/2015 | ........ A61M 5/31566 |

* cited by examiner

ACTIVATION MECHANISM FOR A MEDICAMENT DELIVERY DEVICE AND A MEDICAMENT DELIVERY DEVICE USING THE ACTIVATION MECHANISM

CROSS REFERENCE TO RELATED APPLICATIONS

The present application is a U.S. National Phase Application pursuant to 35 U.S.C. § 371 of International Application No. PCT/EP2016/075646 filed Oct. 25, 2016, which claims priority to Swedish Patent Application No. 1551475-5 filed Nov. 13, 2015. The entire disclosure contents of these applications are herewith incorporated by reference into the present application.

TECHNICAL FIELD

The present disclosure relates to an activation mechanism for a medicament delivery device and in particular to an activation mechanism requiring the actuation of a first and a second activation member to unlock a drive member.

BACKGROUND

There are numerous devices for delivering medicament on the market where the medicament is arranged in a container, such as a syringe, a cartridge or the like, and wherein the medicament is ejected through a delivery member, such as a needle or a nozzle, by having a movable stopper, inside the container, exert a pressure on medicament via a spring-biased drive member, which acts on the stopper.

A group of medicament delivery devices are defined as auto-injectors, wherein at least one of the steps of a delivery sequence is performed automatically, through a spring-biased mechanism, as a consequence of the user pressing a button or as a consequence of a previous mechanism reaching a certain stage. The steps that may be automatically activated are normally skin penetration by the delivery member, e.g. a needle, medicament delivery, and/or delivery member retraction.

In the case of automatic delivery of a medicament, a drive member, such as a plunger rod, often needs to be spring-biased, but prevented from moving until the appropriate moment. In some cases the user may determine when it is time to administrate the medicament. In other cases the medicament may be delivered when the needle has reached a certain depth after penetrating the skin.

There are numerous ways of achieving a two-step activation of a delivery device. U.S. Pat. No. 5,137,516 discloses an example of a device which requires preparation to arm a trigger button. In a first step an internal shaft and a sleeve assembly (which contains a syringe) are moved within an external casing. This movement compresses a button spring and moves a retention clip upwardly toward an actuating button. During the movement, arms of the actuating button move into slots of the retention clip. At the end of this movement, flared parts of the arms of the button are adjacent the ends of the slots of the retention clip. Actuation of the actuating button forces the flared portions of the button arms into the slots of the retention clip, thereby separating arms of the retention clip. Depression of the button, without the movement of the internal shaft, would not be sufficient to move the flared portions into the slots, the downward travel of the button being restricted by arms of a clip.

An aim of the present disclosure is to provide an alternative activation mechanism in view of prior art. A further aim of the disclosure is to provide a space-saving activation mechanism wherein longitudinal actuation of activation members leads to a release of a drive member. By means of the present disclosure a spring-biased drive member may be held by a locking unit which is laterally moved by longitudinal actuation of the activation members of the device. The solution saves space inside a casing of the medicament delivery device, which space may be used for indication mechanisms, drive springs, etc.

SUMMARY

An object of the present disclosure is to provide a medicament delivery device wherein the drawbacks of the state of the art devices are remedied.

In the present application, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

Also, if nothing else is stated, in the following description wherein the mechanical structure of the device and the mechanical interconnection of its components is described, the device is in an initial non-activated or non-operated state.

An embodiment of the present disclosure relates to an activation mechanism for a medicament delivery device, which activation mechanism comprises a housing elongated along a generally longitudinal axis, having a proximal end and a distal end, a spring-biased, longitudinally movable drive member, a locking unit, movable relative to the housing, from a locked position, in engagement with said drive member, preventing longitudinal movement of said drive member, to an unlocked position, disengaged from said drive member, allowing longitudinal movement of said drive member, a first activation member movable relative to the housing between a first initial position and a first activation position, a second activation member movable relative to the housing between a second initial position and a second activation position, wherein the locking unit comprises a key member, movable relative to the locking unit from a neutral position to a cooperating position, and wherein the first activation member and the second activation member are configured to move the locking unit from the locked position to the unlocked position when the first activation member and the second activation member are moved to the first activation position and to the second activation position, respectively.

In an aspect of the embodiment, the actuation of the first activation member moves the first activation member from the first initial position to the first activation position, and a combined actuation of the second activation member moves the second activation member from the second initial position to the second activation position, such that the first activation member and the second activation member cooperate in interacting with the key member to move the key member from the neutral position to the cooperating position and to move the locking unit from the locked position to the unlocked position.

In an aspect of the embodiment the key member comprises a first surface for interacting with the first activation member, which first surface is generally orthogonal in relation to a direction of movement of the first activation member such that movement of the first activation member relative to the housing can move the key member from the neutral position to the cooperating position.

In an aspect of the embodiment, movement of the key member relative to the locking unit is generally orthogonal to the movement of the locking unit relative to the housing.

In an aspect of the embodiment, movement of the key member relative to the locking unit is longitudinal and the movement of the locking unit relative to the housing is generally lateral.

In an aspect of the embodiment the key member is laterally fixed relative to the locking unit and the locking unit is longitudinally fixed relative to the housing.

In an aspect of the embodiment the key member comprises a second surface for interacting with the second activation member, which surface is slanted in a longitudinal-lateral plane, and in relation to a direction of movement of the second actuation member, such that actuation of the second activation member may cause an interaction with the second surface such that a lateral force towards the unlocked position is exerted on the locking unit.

In an aspect of the embodiment, an end surface of the second activation member is adjacent second surface of the key member when the key member is in the neutral position and the second activation member is in the second activation position.

In an aspect of the embodiment, movement of the key member from the neutral position to the cooperating position is a movement towards the second activation member.

In an aspect of the embodiment the first activation member and the second activation member comprise a first activation member extension and a second activation member extension, respectively, protruding outside the housing for manual actuation.

In an aspect of the embodiment the housing comprises a chassis, fixedly attached to the housing, which chassis comprises first guide tracks, restricting the movement of the first activation member, the second activation member and the locking unit to bi-directional movement relative to the chassis, and to the housing, and the locking unit comprises second guide tracks, restricting the movement of the key member to bi-directional movement relative to the locking unit.

In an aspect of the embodiment the housing comprises first guide tracks, restricting the movement of the first activation member, the second activation member and the locking unit to bi-directional movement relative to the housing, and the locking unit comprises second guide tracks, restricting the movement of the key member to bi-directional movement relative to the locking unit.

In an aspect of the embodiment the first activation member extension comprises a push button and the second activation member extension comprises a needle guard, and actuation of the push button causes proximal movement of the first activation member towards the first activation position, and actuation of the proximal needle guard causes distal movement of the second activation member towards the second activation position.

In an aspect of the embodiment the first activation member extension comprises a needle guard and the second activation member extension comprises a push button, and actuation of the push button causes proximal movement of the second activation member towards the second activation position, and actuation of the needle guard causes distal movement of the first activation member towards the first activation position.

A further embodiment relates to a medicament delivery device comprising an activation mechanism according to the present disclosure.

BRIEF DESCRIPTION OF THE DRAWINGS

The figures below disclose an embodiment of the present disclosure for illustrational purposes only. In particular, the disclosure within the figures is not meant to limit the range of protection of the present disclosure. The embodiment shown may be modified in different ways within the scope of the claims.

DETAILED DESCRIPTION

Figure 1:
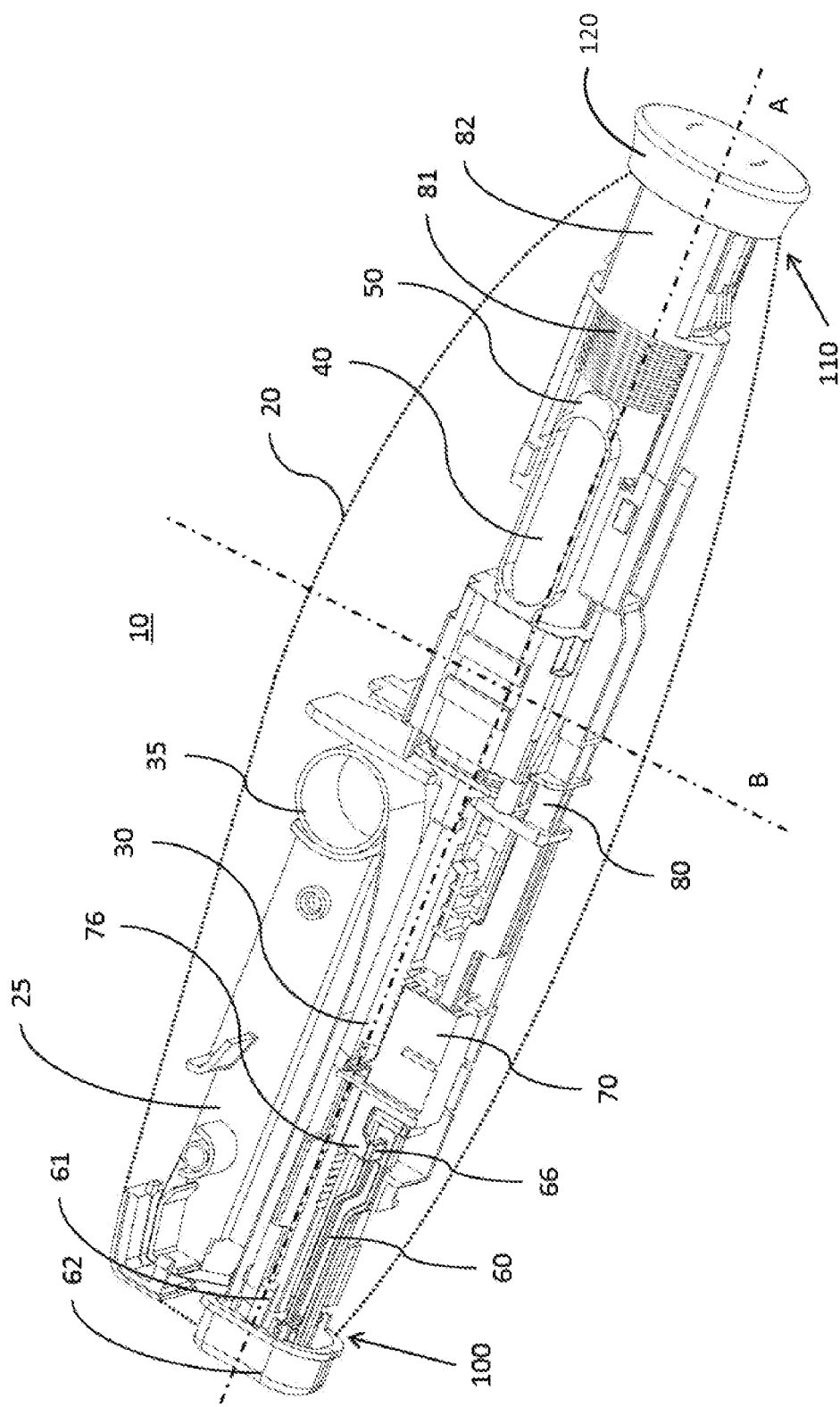
FIG. 1 is a perspective view of a medicament delivery device comprising an activation mechanism according to the disclosure.

FIG. 1 shows a perspective view of a medicament delivery device 10, having a housing 20 elongated along a generally longitudinal axis A, which housing has a proximal end 110 and a distal end 100. The housing 20 disclosed in FIG. 1 is only visualized by a dotted line to show the general outline of the housing. A lateral axis B is orthogonal to the longitudinal axis A.

A drive member, such as a plunger rod, is configured to be activated to exert a force on a stopper (not shown) in a medicament container 40, held in a container holder 50. The driver member is spring-biased and longitudinally movable relative to the housing. When activated, the exerted force creates a pressure on a liquid medicament in the medicament container, such that the medicament may be expelled through a delivery member (not shown) initially covered and protected by cap 120, which delivery member may be a nozzle, a mouthpiece, a needle, or similar, for delivering the medicament to an area of treatment on, or in, a patient's body. The force is exerted by an energy accumulating member 35, such as a spring. In the embodiment shown, the energy accumulating member 35 is a flat spiral spring, e.g. a clock spring, or a constant force spring, but the activation mechanism could also be realized using a coil spring, a variable force spring or by pressurized fluid or electrical means, for instance arranged inside the drive member 30.

The activation mechanism according to the present disclosure comprises, apart from the aforementioned drive member 30, a locking unit 70, movable relative to the housing 20, a first activation member 60 movable relative to the housing, and a second activation member 80 movable relative to the housing. The locking unit further comprises a key member 90 (FIG. 2), movable relative to the locking unit 70.

The first activation member 60 and the second activation member 80 comprise a first activation member extension and a second activation member extension, respectively, protruding outside the housing 20 for manual actuation by a user. In the embodiment shown in the figures, the first activation member extension 60 comprises a push button 62 and the second activation member comprises a needle guard 82. However, as readily recognized by a skilled person, the activation mechanism could be turned 180 degrees around a lateral axis so that the first activation member extension would comprise the needle guard, and so that the second activation member extension would comprise the push button. The principle of operation of the activation mechanism would still be the same as described herein.

Figure 2:
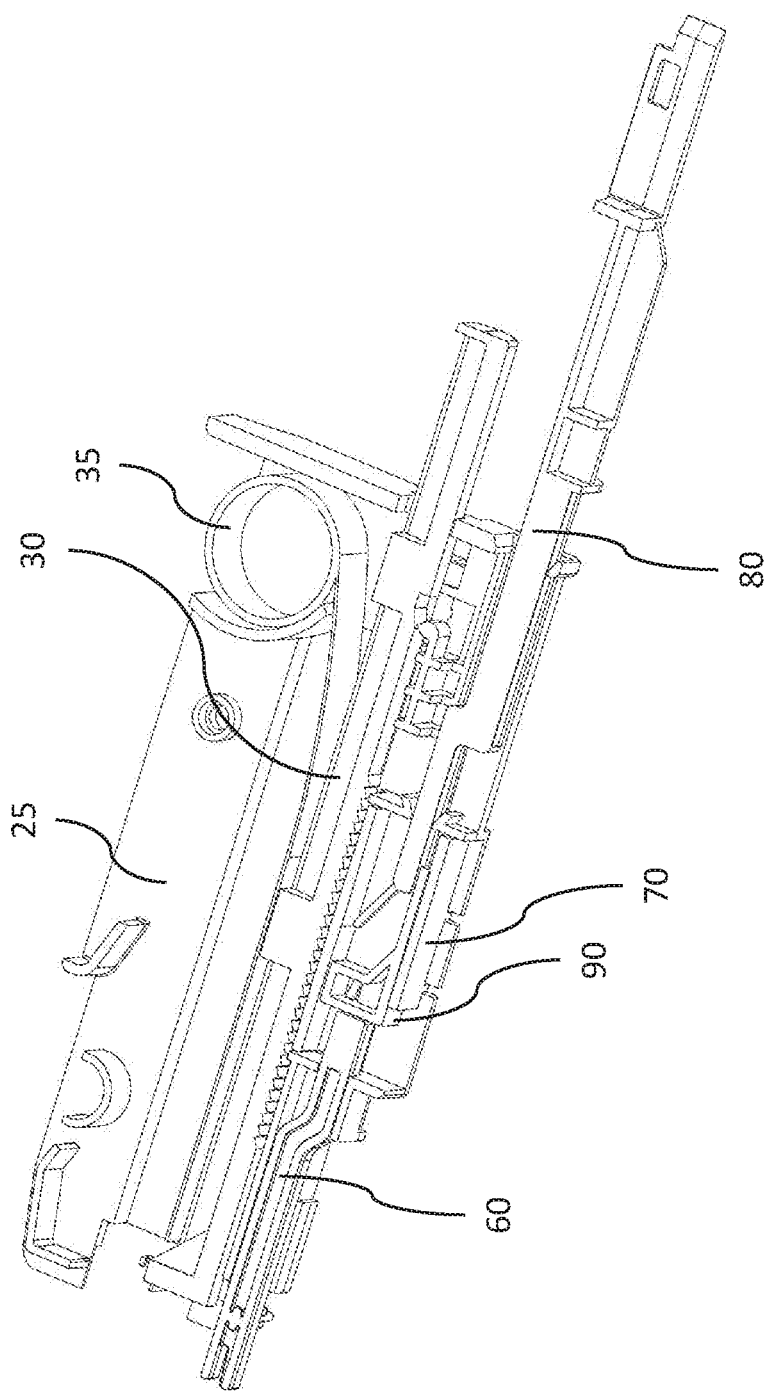
FIG. 2 is a perspective view of the activation mechanism.
Figure 6:
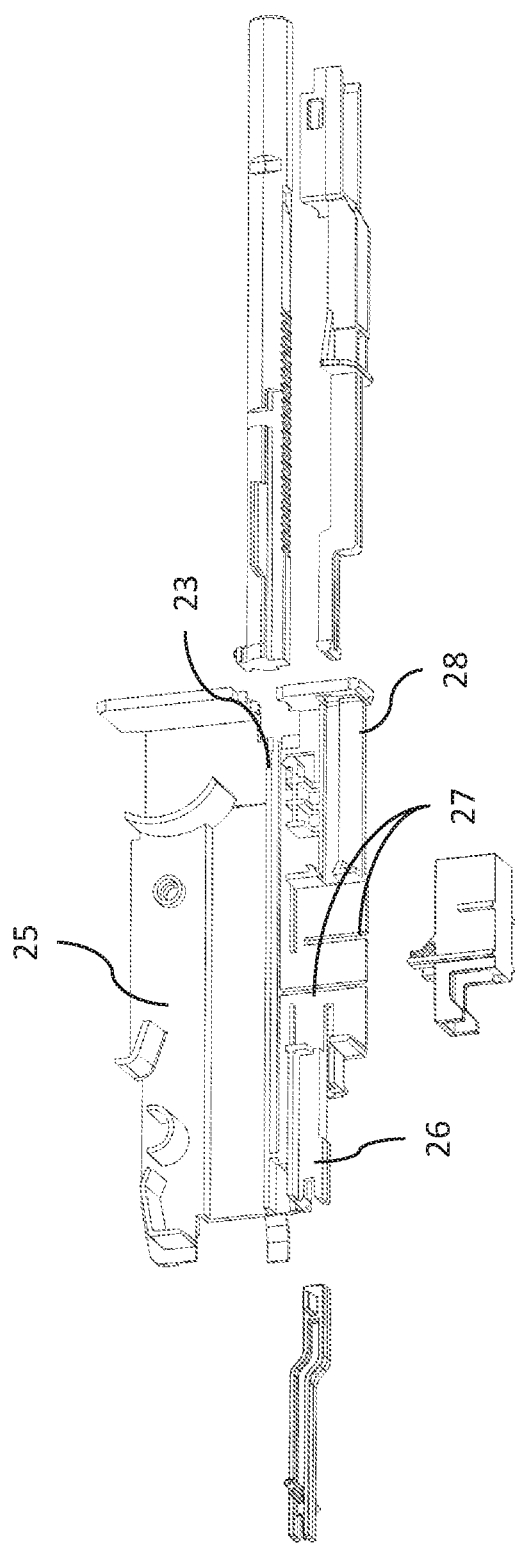
FIG. 6 an exploded perspective view of the activation mechanism and a chassis.

Turning to FIG. 2, the activation mechanism is shown in more detail in a cross-sectional view. The housing 20 may comprise a chassis 25, fixedly attached to the housing, having first guide tracks 26, 28, 27 (FIG. 6) configured to restrict movement of the first activation member 60, the second activation member 80 and the locking unit 70, respectively, to bi-directional movement relative to the chassis 25, and to the housing 20.

The chassis 25 further comprises a drive member guide track 23 configured to restrict movement of the drive member 30 to bidirectional longitudinal movement relative to the chassis, and to the housing.

The locking unit 70 further comprises second guide tracks 79 (FIG. 4), configured to restrict movement of the key member 90 to bi-directional longitudinal movement relative to the locking unit 70. The key member 90 is thus laterally fixed relative to the locking unit 70.

It should be noted that the chassis 25, shown in the figures, constitutes only a first half of the full chassis. A second half of the chassis is configured to mate with the first half to sandwich the components of the activation mechanism there between, inside the full chassis.

In another embodiment, the first guide tracks 26, 28, 27 and the drive member guide track 23 are instead configured as integral structures on the inner surface of the housing 20, such that the chassis 25 may be dispensed with. In this way, the number of components may be reduced, which lowers costs and may simplify assembly of the medicament delivery device.

The first activation member 60 is movable relative to the housing 20 between a first initial position and a first activation position and the second activation member 80 is movable relative to the housing 20 between a second initial position and a second activation position. In FIG. 2 the first activation member 60 and the second activation member 80 are shown in the first initial position and in the second initial position, respectively.

The locking unit 70 is movable relative to the housing 20, from a locked position, in engagement with said drive member 30, preventing longitudinal movement of said drive member 30, to an unlocked position, disengaged from said drive member 30, and allowing longitudinal movement of said drive member 30. Consequently, activation of the medicament delivery device is the operation of moving the locking unit 70 from the locked position to the unlocked position such that the drive member 30 is released to move longitudinally under influence of the energy accumulating member 35.

As described above, the locking unit 70 comprises a key member 90, movable relative to the locking unit 70 from a neutral position to a cooperating position.

The neutral position is defined as a position of the key member 90, relative to the locking unit 70, in which position the key member 90 is prevented from being displaced, relative to the locking unit 70, by the second activation member 80, because the second activation member 80 cannot move further than the second activation position.

The cooperating position is defined as a position of the key member 90, relative to the locking unit 70, in which position the key member 90 is prevented from being displaced, relative to the locking unit 70, by the first activation member 60, because the first activation member 60 cannot move further than the first activation position.

Actuation of the first activation member 60 moves the first activation member from the first initial position to the first activation position, and a combined actuation of the second activation 80 member moves the second activation member 80 from the second initial position to the second activation position, such that the first activation member 60 and the second activation member 80 cooperate in interacting with the key member 90 to move the key member 90 from the neutral position to the cooperating position and to move the locking unit 70 from the locked position to the unlocked position.

Actuation of an activation member is defined as a user exerting a pressure on the activation member from outside the housing 20 and thereby moving the activation member from the initial position to the activation position. Actuation may also be the act of maintaining the exerted pressure on the activation member in question. Combined actuation of the activation members is consequently defined as moving both the first activation member 60 and the second activation member 80 to the first activation position and to the second activation position, respectively, and maintaining the pressure on both activation members at the same time, at least for a brief period of time, regardless of which activation member moves first, i.e. regardless of which activation member is first actuated.

Figure 3:
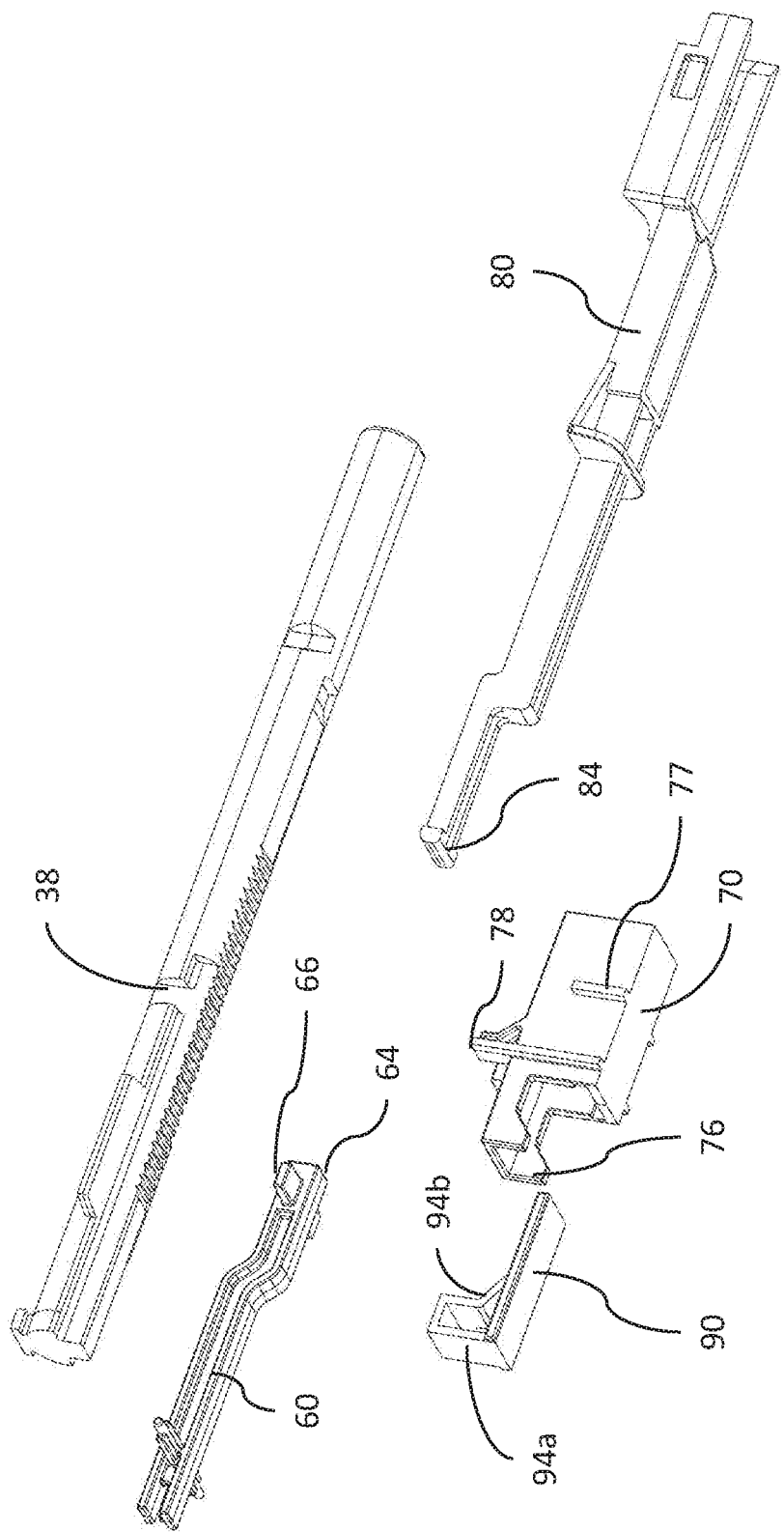
FIG. 3 is an exploded perspective view of the activation mechanism.

In FIG. 3, an exploded view of the activation mechanism shows that the first activation member 60 is arranged with a proximally directed surface 64. Said proximally directed surface 64 may interact with a distally directed first surface 94a of the key member 90. If the key member 90 moves laterally relative to the housing 20, the first activation member 60 may, via the surface 64, slide relative to the first surface 94a.

The first activation member 60 further comprises a first blocking member 66. The first blocking member 66 abuts a second blocking member 76 of the locking unit 70 and prevents movement of the locking unit 70 from the locked position to the unlocked position when the first activation member 60 is in the first initial position (FIG. 1).

The second activation member 80 comprises a distally directed end surface 84, which end surface 84 may interact with a second surface 94b of the key member 90, when the key member 90 is in the cooperating position. Said second surface 94b is slanted in a longitudinal-lateral plane spanned by the longitudinal and lateral axes A and B, and also slanted in relation to a direction of movement of the second actuation member 80.

The locking unit 70 comprises a first engagement member 78 and the spring-biased drive member 30 comprises a second engagement member 38. The first engagement member 78 may interact with the second engagement member 38 when the locking unit 70 is in the locked position. The interaction causes the locking unit 70 to be in engagement with the drive member 30, thereby preventing longitudinal movement of the drive member 30.

The locking unit 70 further comprises a first track follower 77 which mates with the first guide tracks 27 of the chassis 25, which first guide tracks 27 are arranged laterally. In a similar way, the first track follower 77 may alternatively mate with the first guide tracks 27 of the housing 20 in the embodiment without a chassis 25. The locking unit 70 is therefore restricted to bi-directional, lateral movement in relation to the housing 20.

Figure 4:
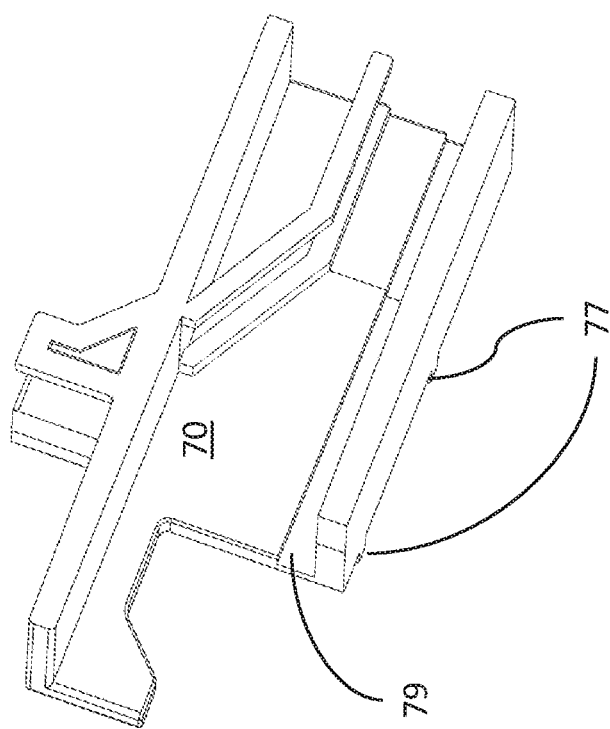
FIG. 4 is an exploded cross-sectional view of a locking unit and a key member of the disclosure.
Figure 4:
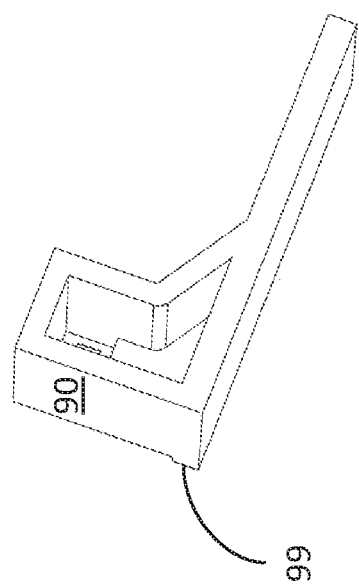

Referring to FIG. 4, the locking unit 70 and the key member 90 are shown in an exploded cross-sectional view. The second guide track 79 is a longitudinal track on the inner surface of the locking unit 70. The key member 90 comprises a longitudinal second track follower 99. The key member 90 is therefore restricted to bi-directional, longitudinal movement relative to the locking unit 70.

Accordingly, movement of the key member 90 relative to the locking unit 70 is generally orthogonal to the movement of the locking unit 70 relative to the housing 20. More specifically, movement of the key member 90 relative to the locking unit 70 is generally longitudinal and movement of the locking unit 90 relative to the housing 20 is generally lateral.

A distal end and a proximal end of the locking member 70 are open. The key member 90 is freely movable along the second guide track 79. The key member 90 is thus prevented from exiting the locking unit 70, by the open distal and proximal ends, by the first activation member 60 and the second activation member 80, respectively, as shown in FIG. 2.

Figure 5A:
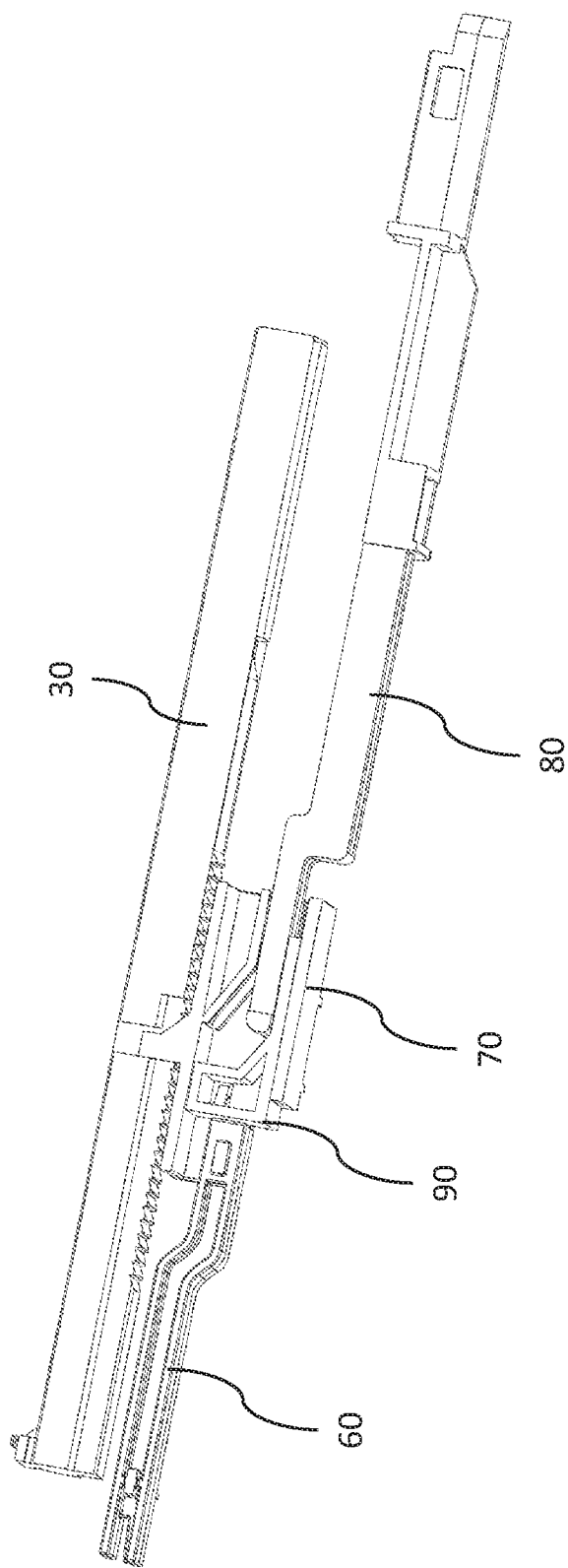
FIG. 5*a* is a perspective cross-sectional view of a state of operation of the activation mechanism.
Figure 5B:
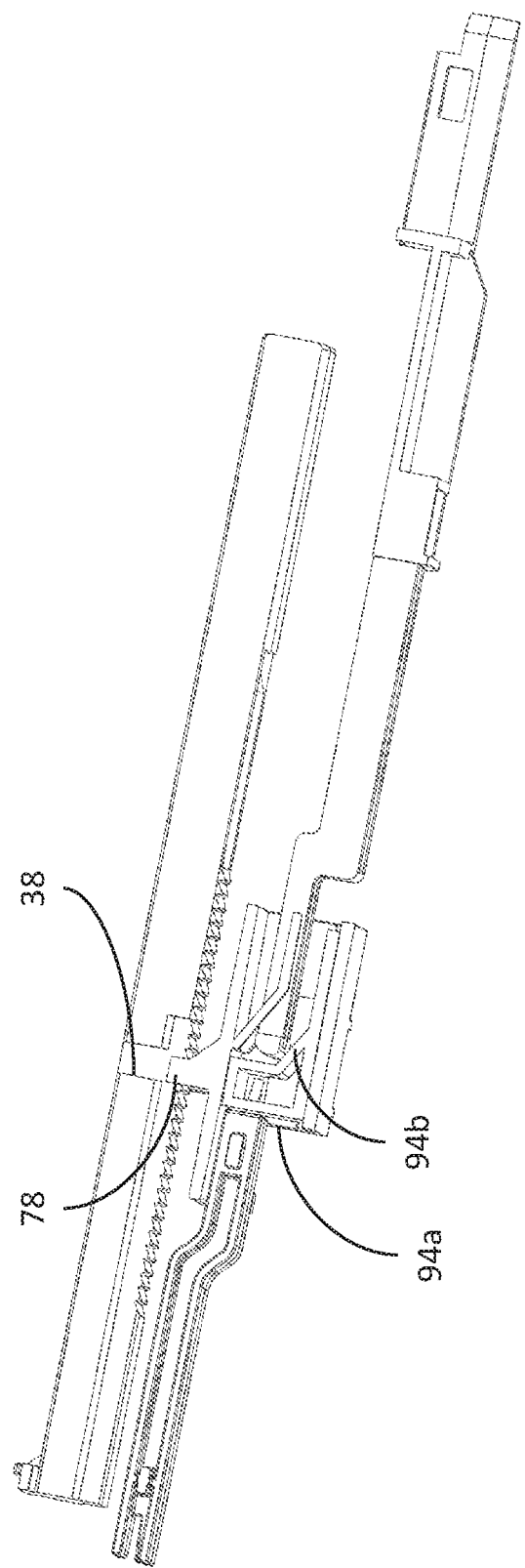
FIG. 5*b* is a perspective cross-sectional view of a subsequent state of operation of the activation mechanism.
Figure 5C:
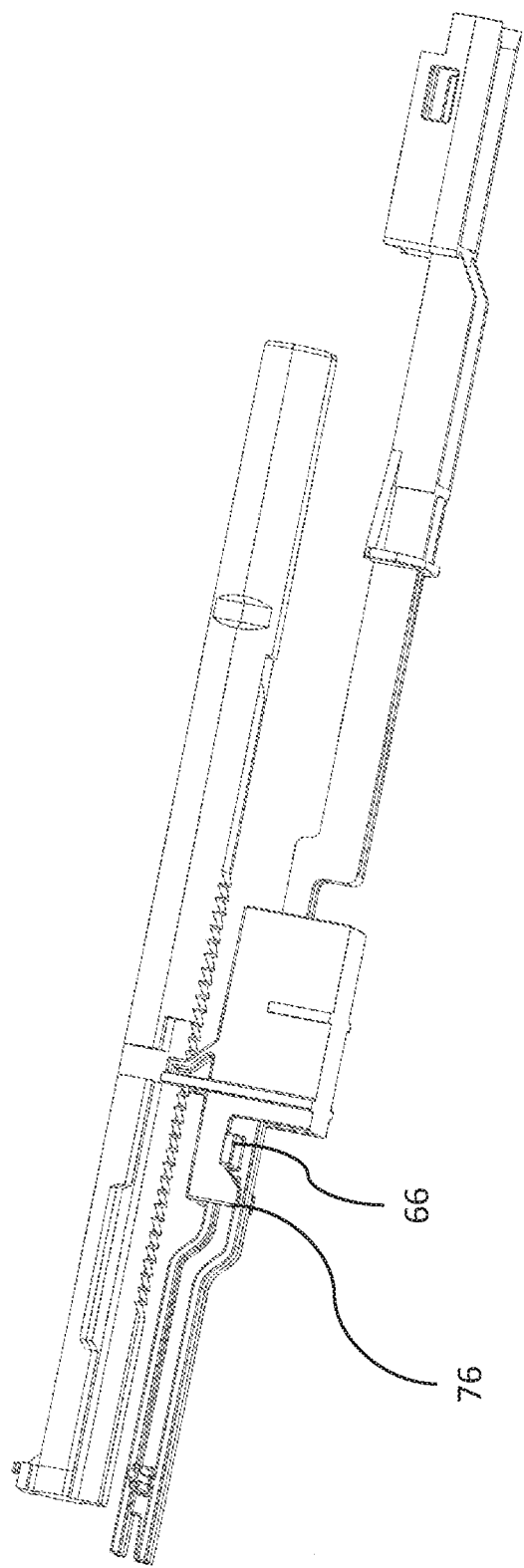
FIG. 5*c* is a perspective view of the subsequent state of operation of the activation mechanism of FIG. 5*b*.

The function of the activation mechanism will now be described in more detail, referring to FIGS. 5a-5c. Initially, the first activation member 60 is in the first initial position and the second activation member 80 is in the second initial position. See FIG. 2. A user actuates an activation member by exerting a manual force on either the first activation member 60 or on the second activation member 80, which will cause movement of the respective activation member. Resilient elements, or springs, may be arranged to return the activation members to the respective initial positions if the user removes the exerted force. As an example of the embodiment shown in the drawings (FIG. 1), the second activation member extension 82 may be arranged with a spring 81 and the first activation member extension may be arranged with resilient elements 61. The resilient elements 61 may for instance be arranged in a force-biased interaction with the housing 20 or the chassis 25, so that actuation of the first and the second activation member extensions causes a tensioning of the resilient elements 61 of the first activation member extension 62 and also a tensioning of the spring 81 of the second activation member extension 82, and wherein return movement of the first activation member extension 62 and the second activation member extension 82 is caused by a return movement of the resilient elements 61 and the spring 81, respectively, as they return from a tensioned state to a more relaxed state when the user stops actuating the activation member extensions.

If the first activation member 60 is actuated on its own i.e. no actuation of the second activation member 80, the first activation member 60 will move proximally to the first activation position, by which movement the first blocking element 66 of the first activation member 60 is moved out of contact with the second blocking element 76 of the locking unit 70.

If the key member 90 is currently located in the neutral position, the key member 90 will be moved proximally, to the cooperating position, by interaction of the proximally directed surface 64 of the first activation member 60 with the distally directed surface 94a of the key member 90.

On the other hand, if the key member 90 is currently located in the cooperating position, the first activation member 60 will move proximally to the first activation position, in which position the proximally directed surface 64 will be adjacent the distally directed surface 94a.

In case the second activation member 80 is actuated on its own, i.e. no actuation of the first activation member 60, the second activation member 80 will move distally to the second activation position. See FIG. 5a, wherein the first activation member 60 is in the first initial position, the second activation member 80 has been moved to the second activation position, the key member 90 is in the neutral position, and the locking unit 70 is in the locked position.

If the key member 90 is currently located in the neutral position, the second activation member 80 will move distally to the second activation position, in which position the end surface 84 of the second activation member 80 will be adjacent the second surface 94b of the key member 90.

On the other hand, if the key member 90 is currently located in the cooperating position, the key member 90 will be moved distally, to the neutral position, by interaction of the end surface 84 with the second surface 94b.

In case the first activation member 60 and the second activation member 80 are actuated in combination (FIGS. 5b and 5c), the first activation member 60 and the second activation member 80 are moved to the first activation position and to the second activation position, respectively. Due to the actuation of the first activation member 60, i.e. movement and maintained pressure on the first activation member 60, the key member 90 will be moved towards the cooperating position, which is a movement towards the second activation member 80. However, since the second activation member 80 is either already in the second activation position, wherein the end surface 84 is adjacent the second surface 94b, or moving towards the second activation position, movement of the key member 90 towards the cooperating position, or maintained pressure on the key member 90 in the cooperating position, will cause the end surface 84 of the second activation member to begin sliding against the second surface 94b of the key member 90, which second surface 94b is slanted in relation to the longitudinal axis A and to the lateral axis B. Consequently, since the key member 90 is restricted to bi-directional longitudinal movement in relation to the locking unit 70, the combined interaction of the proximally directed surface 64 with the distally directed surface 94a, and the end surface 84 with the second surface 94b, will cause a lateral component force between the slanted second surface 94b and the end surface 84, which lateral force will be transferred from the key member 90 to the locking unit 70 via the second guide tracks 77. The lateral force will thus push the locking unit 70 from the locked position to the unlocked position, thereby disengaging the first engagement member 78 from the second engagement member 38, releasing the spring-biased plunger rod for movement.

Thus it can be seen that the sequence of actuation of the first activation member 60 and the second activation member 80 is irrelevant to the operation of the activation mechanism.

If the first activation member 60 is actuated before the second activation member 80 is actuated, the key member 90 will be in the cooperating position and will therefore not move longitudinally relative to the locking unit when the second activation member 80 is actuated because the key member 90 is held in the cooperating position by the first activation member 60, on which pressure is maintained during actuation. Instead the locking unit 70 will move laterally as the end surface 84 of the second activation member 80 slides against the slanted second surface 94b of the key member 90.

If the second activation member 80 is actuated before the first activation member 60, the key member 90 will be in the neutral position and will therefore move proximally relative to the locking unit when the first activation member 60 is actuated, but since the end surface 84 of the second activation member 80 is held in position adjacent the second surface 94b, by maintained pressure during actuation, the locking unit 70 will move laterally as the end surface 84 of the second activation member 80 slides against the slanted second surface 94b of the key member 90.

As the locking unit moves laterally, the distally directed surface 94a will also slide against the proximally directed surface 64.

Obviously, simultaneous movement of the first activation member 60 and the second activation member 80 towards their respective activation positions will also result in lateral movement of the locking unit 70 towards the unlocked position.

In the unlocked position, the spring-biased drive member 30 is released to move proximally and expel the contents of a container of a medicament delivery device.

The invention claimed is:

1. An activation mechanism for a medicament delivery device, where the activation mechanism comprises:
    a housing elongated along a generally longitudinal axis, the housing having a proximal end and a distal end;
    a spring-biased drive member, longitudinally movable relative to the housing;
    a track axially fixed relative to the housing;
    a locking unit, engaged with the track and movable only in an axial direction relative to the housing, from a locked position, in engagement with said spring-biased drive member, preventing longitudinal movement of said spring-biased drive member, to an unlocked position, disengaged from said spring-biased drive member, allowing longitudinal movement of said spring-biased drive member;
    a first activation member movable relative to the housing between a first initial position and a first activation position;
    a second activation member movable relative to the housing between a second initial position and a second activation position;
    wherein the locking unit comprises a key member, movable relative to the locking unit from a neutral position to a cooperating position, and wherein the first activation member and the second activation member are configured to move the locking unit, by interaction with the key member, from the locked position to the unlocked position when the first activation member and the second activation member are moved to the first activation position and to the second activation position, respectively, and wherein actuation of the first activation member moves the first activation member from the first initial position to the first activation position, and wherein combined actuation of the second activation member moves the second activation member from the second initial position to the second activation position, such that the first activation member and the second activation member cooperate in interacting with the key member to move the key member to the cooperating position and to move the locking unit from the locked position to the unlocked position.

2. The activation mechanism for a medicament delivery device according to claim 1, wherein the key member comprises a first surface for interacting with the first activation member, where the first surface is generally orthogonal in relation to a direction of movement of the first activation member such that movement of the first activation member relative to the housing may move the key member from the neutral position to the cooperating position.

3. The activation mechanism for a medicament delivery device according to claim 2 wherein movement of the key member relative to the locking unit is longitudinal and wherein the movement of the locking unit relative to the housing is generally lateral.

4. The activation mechanism for a medicament delivery device according to claim 3, wherein the first activation member and the second activation member are longitudinally movable.

5. The activation mechanism for a medicament delivery device according to claim 4 wherein the key member is laterally fixed relative to the locking unit and wherein the locking unit is longitudinally fixed relative to the housing.

6. The activation mechanism for a medicament delivery device according to claim 5, wherein the key member comprises a second surface for interacting with the second activation member, which second surface is slanted in a longitudinal-lateral plane and in relation to a direction of movement of the second actuation member, such that actuation of the second activation member may cause an interaction with the second surface such that a lateral force towards the unlocked position is exerted on the locking unit.

7. The activation mechanism for a medicament delivery device according to claim 6, wherein an end surface of the second activation member is adjacent second surface of the key member when the key member is in the neutral position and the second activation member is in the second activation position.

8. The activation mechanism for a medicament delivery device according to claim 7, wherein movement of the key member from the neutral position to the cooperating position is a movement generally towards the second activation member.

9. The activation mechanism for a medicament delivery device according to claim 1, wherein the first activation member comprises a first blocking member, where the first blocking member abuts a second blocking member of the locking unit and prevents movement of the locking unit from the locked position to the unlocked position when the first activation member is in the first initial position.

10. The activation mechanism for a medicament delivery device according to claim 1, wherein the housing comprises a chassis that is fixedly attached to the housing, where the chassis comprises first guide tracks restricting the movement of the first activation member and the second activation member to bi-directional movement relative to the chassis, and to the housing, and wherein the locking unit comprises second guide tracks, restricting the movement of the key member to bi-directional movement relative to the locking unit.

11. The activation mechanism for a medicament delivery device according to claim 1, wherein the housing comprises first guide tracks restricting the movement of the first activation member and the second activation member to bi-directional movement relative to the housing, and wherein the locking unit comprises second guide tracks, restricting the movement of the key member to bi-directional movement relative to the locking unit.

12. The activation mechanism for a medicament delivery device according to claim 1, wherein the first activation member and the second activation member comprise a first activation member extension and a second activation member extension, respectively, protruding outside the housing for manual actuation.

13. The activation mechanism for a medicament delivery device according to claim 12, wherein the first activation member extension comprises a push button and the second activation member extension comprises a needle guard, and wherein actuation of the push button causes proximal movement of the first activation member towards the first activation position, and wherein actuation of the needle guard causes distal movement of the second activation member towards the second activation position.

14. The activation mechanism for a medicament delivery device according to claim 12, wherein the first activation member extension comprises a push button needle guard and the second activation member extension comprises a needle guard, and wherein actuation of the push button causes proximal movement of the second activation member towards the second activation position, and wherein actuation of the needle guard causes distal movement of the first activation member towards the first activation position.

15. A medicament delivery device comprising an activation mechanism comprising:
 a housing elongated along a generally longitudinal axis, the housing having a proximal end and a distal end;
 a cap attached to the proximal end;
 a medicament container; and
 an activation member comprising,
 i) a spring-biased drive member, longitudinally movable relative to the housing and operatively engaged with the medicament container;
 ii) a track axially fixed relative to the housing;
 iii) a locking unit, engaged with the track and movable only in an axial direction relative to the housing, from a locked position, in engagement with said spring-biased drive member, preventing longitudinal movement of said spring-biased drive member, to an unlocked position, disengaged from said spring-biased drive member, allowing longitudinal movement of said spring-biased drive member;
 iv) a first activation member movable relative to the housing between a first initial position and a first activation position; and
 v a second activation member movable relative to the housing between a second initial position and a second activation position; and
 wherein the locking unit comprises a key member, movable relative to the locking unit from a neutral position to a cooperating position, and wherein the first activation member and the second activation member are configured to move the locking unit, by interaction with the key member, from the locked position to the unlocked position when the first activation member and the second activation member are moved to the first activation position and to the second activation position, respectively, and wherein actuation of the first activation member moves the first activation member from the first initial position to the first activation position, and wherein combined actuation of the second activation member moves the second activation member from the second initial position to the second activation position, such that the first activation member and the second activation member cooperate in interacting with the key member to move the key member to the cooperating position and to move the locking unit from the locked position to the unlocked position.

16. The medicament delivery device according to claim 15, wherein the first activation member and the second activation member comprise a first activation member extension and a second activation member extension, respectively, protruding outside the housing for manual actuation.

17. The medicament delivery device according to claim 16, wherein the first activation member extension comprises a push button and the second activation member extension comprises a needle guard, and wherein actuation of the push button causes proximal movement of the first activation member towards the first activation position, and wherein actuation of the needle guard causes distal movement of the second activation member towards the second activation position.

18. The medicament delivery device according to claim 16, wherein the first activation member extension comprises a push button needle guard and the second activation member extension comprises a needle guard, and wherein actuation of the push button causes proximal movement of the second activation member towards the second activation position, and wherein actuation of the needle guard causes distal movement of the first activation member towards the first activation position.

19. An activation mechanism contained within a housing having a longitudinal axis, a proximal end and a distal end, the activation mechanism comprising;
 a spring-biased drive member, longitudinally movable relative to the housing;
 a locking unit, movable relative to the housing, from a locked position, in engagement with said spring-biased drive member, preventing longitudinal movement of said spring-biased drive member, to an unlocked position, disengaged from said spring-biased drive member, allowing longitudinal movement of said spring-biased drive member;
 a first activation member movable relative to the housing between a first initial position and a first activation position;
 a second activation member movable relative to the housing between a second initial position and a second activation position;
 wherein the locking unit comprises a key member movable relative to the locking unit from a neutral position to a cooperating position, and wherein the first activation member and the second activation member are configured to move the locking unit, by interaction with the key member, from the locked position to the unlocked position when the first activation member and the second activation member are moved to the first activation position and to the second activation position, respectively, and wherein actuation of the first activation member moves the first activation member from the first initial position to the first activation position, and wherein combined actuation of the second activation member moves the second activation member from the second initial position to the second activation position, such that the first activation member and the second activation member cooperate in interacting with the key member to move the key member to the cooperating position and to move the locking unit from the locked position to the unlocked position, wherein movement of the key member relative to the locking unit is longitudinal and wherein the movement of the locking unit relative to the housing is generally lateral, and wherein the first activation member comprises a first blocking member, which first blocking member abuts a second blocking member of the locking unit and prevents movement of the locking unit from the locked position to the unlocked position when the first activation member is in the first initial position.

20. The activation mechanism according to claim 19, wherein the first activation member and the second activation member are longitudinally movable and the key member is laterally fixed relative to the locking unit and wherein the locking unit is longitudinally fixed relative to the housing.

\* \* \* \* \*